United States Patent [19]

Yamamoto et al.

[11] Patent Number: 5,059,587

[45] Date of Patent: Oct. 22, 1991

[54] PHYSIOLOGICALLY ACTIVE PEPTIDE COMPOSITION FOR NASAL ADMINISTRATION

[75] Inventors: Nakayuki Yamamoto; Hideo Sakakibara; Kimio Mizuno, all of Shizuoka, Japan

[73] Assignee: Toyo Jozo Company, Ltd., Shizuoka, Japan

[21] Appl. No.: 221,302

[22] Filed: Jul. 19, 1988

[30] Foreign Application Priority Data

Aug. 3, 1987 [JP] Japan .................................. 62-192658
Nov. 26, 1987 [JP] Japan .................................. 62-296059
Jun. 16, 1988 [JP] Japan .................................. 63-144704

[51] Int. Cl.$^5$ ............................................. A61K 37/02
[52] U.S. Cl. ...................................... 514/12; 514/947; 514/951; 514/970; 514/953
[58] Field of Search ...................... 514/12, 4, 947, 951, 514/953, 959, 970

[56] References Cited

U.S. PATENT DOCUMENTS

| | | | |
|---|---|---|---|
| 4,476,116 | 10/1984 | Anik | 514/15 |
| 4,609,640 | 9/1986 | Morishita | 514/12 |
| 4,690,952 | 9/1987 | Kagatani | 514/3 |

FOREIGN PATENT DOCUMENTS

| | | |
|---|---|---|
| A223359 | 2/1981 | European Pat. Off. . |
| A367513 | 5/1981 | European Pat. Off. . |
| A1122036 | 10/1984 | European Pat. Off. . |
| A3183527 | 6/1986 | European Pat. Off. . |
| A1187433 | 7/1986 | European Pat. Off. . |
| A2193372 | 9/1986 | European Pat. Off. . |
| 2456522 | 12/1980 | France . |

*Primary Examiner*—F. T. Moezie
*Attorney, Agent, or Firm*—Darby & Darby

[57] ABSTRACT

A nasal administration powder composition containing a physiologically active peptide as an active ingredient can be efficiently absorbed through nasal mucosa by the addition of a water-soluble organic acid as an absorption promoter. This composition may further contain a diluent. The water-soluble organic acid used as absorption promoter includes, for example, at least one of succinic acid, tartaric acid, citric acid, fumaric acid, maleic acid, malonic acid, glutaric acid, adipic acid, malic acid, L-glutamic acid, L-aspartic acid, gluconic acid and glucuronic acid.

10 Claims, 4 Drawing Sheets

PHYSIOLOGICALLY ACTIVE PEPTIDE COMPOSITION FOR NASAL ADMINISTRATION

BACKGROUND OF THE INVENTION

This invention relates to a nasal administration powder composition containing a physiologically active peptide as an active ingredient which has been improved in in terms of efficiency of absorption through nasal mucosa.

Peptide hormones such as insulin and calcitonin which are used as clinical drugs at present are susceptible to hydrolysis with enzymes in gastrointestinal tracts and on the wall of gastrointestinal tracts and it is very difficult to have them absorbed through gastrointestinal tracts. Thus, hitherto, they have been administered only by injections.

However, injections often cause pains and are not preferred and other administration methods have been attempted. For example, there have been proposed rectal administration as a suppository [J. Pharm. Pharmacol., 33,334 (1981)], endotracheal administration [Diabetes, 20,552 (1971)] and eyedropping administration (Summary of J. of the Diabetic Society, 237 (1974)]. However, they have not yet been put to practical use because of lower absorption rate than by injections and great variation in absorption.

Some attempts have been made on nasal administration and, for example, a method is known which uses a surface active agent as an absorption promoter [e.g., Japanese Patent Kokai Nos. 59-89619 and 59-130820 and Diabetes, 27,296 (1977)]. However, the drug is liquid and readily runs out after administration. There are further problems that safety and stability of drug are damaged due to addition of the surface active agents and incorporation of microorganisms.

On the other hand, powdered nasal administration preparations have been proposed. A powdered nasal administration preparation was already put to practical use as a preparation for Intal ® (Fujisawa Pharmaceutical Co., Ltd., FISONS plc England) in 1975. Further, a powdered composition for nasal administration containing water absorbing base was proposed as the peptide preparation (Japanese Patent Kokai No. 59-163313). However, this preparation was practically not necessarily excellent since the effective component is not sufficiently absorbed from the nasal cavity.

SUMMARY OF THE INVENTION

The object of this invention is to provide a powdered nasal administration composition containing peptide hormone as an active ingredient which is superior in safety and stability and from which the active ingredient can be fully absorbed through the nasal cavity.

DESCRIPTION OF THE INVENTION

Figure 1:
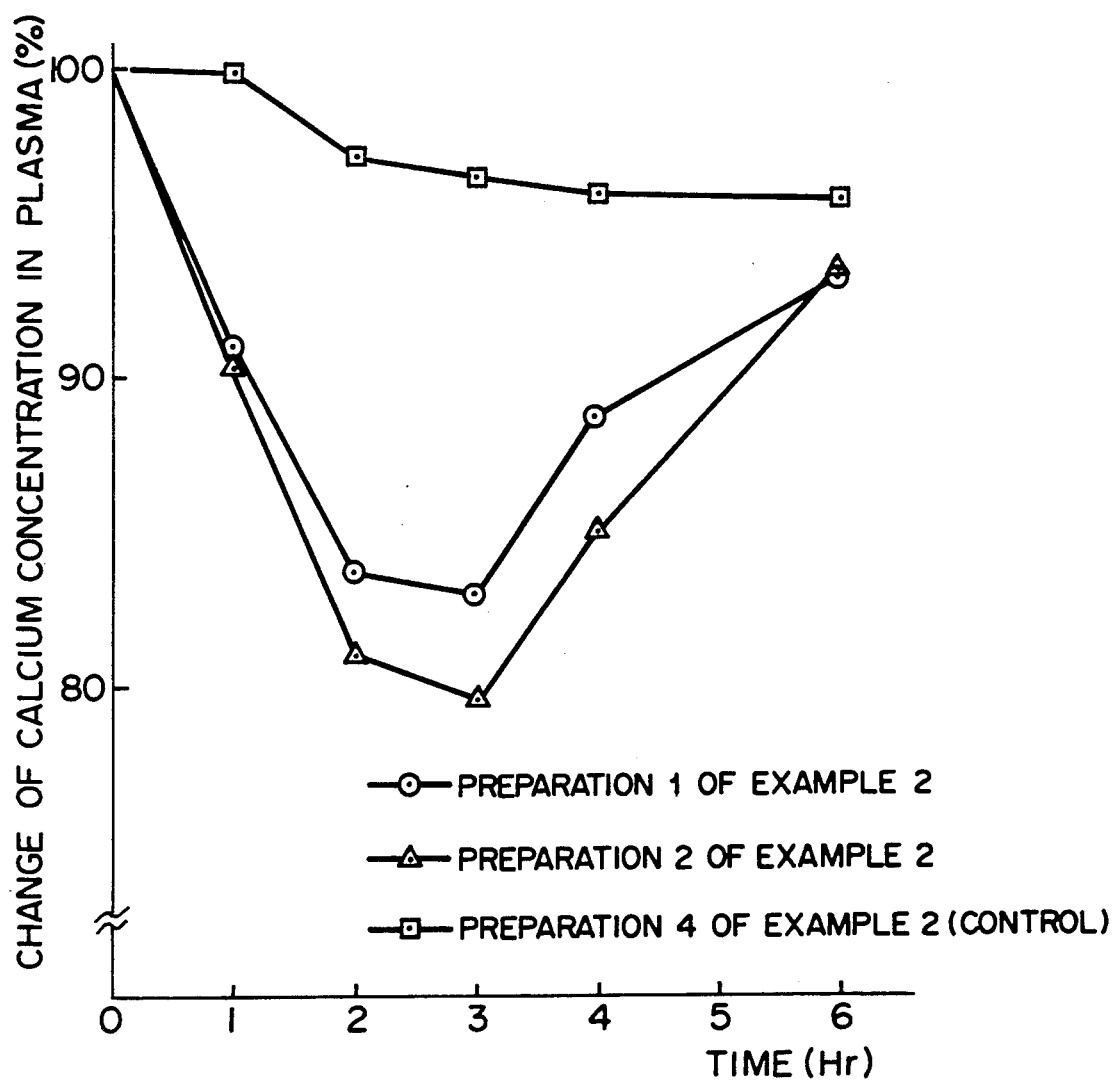
FIG. 1 is a graph which shows changes in calcium concentration in plasma of rabbits when preparations 1 and 2 in Example 2 of this invention and preparation 4 containing no water-soluble organic acid as a control were administered to rabbits, respectively.

The inventors have obtained a powdered preparation containing calcitonin as an active ingredient which is superior in absorption and contains additionally a water-soluble organic acid as an absorption promoter and furthermore a diluent. As a result of further study, they have found powdered preparations for nasal administration which show excellent absorbability for other peptide hormones. This invention is based on this finding.

That is, this invention relates to a nasal administration powdered composition containing a physiologically active peptide as an active ingredient, characterized by containing a water-soluble organic acid as an absorption promoter and, if necessary, a diluent.

The physiologically active peptides which are active ingredients in the composition of this invention include, for example, -peptide hormones, proteins and enzymes which have physiological activity such as calcitonin gene related peptides (CGRP), calcitonin, parathyroid hormone (PTH), insulin, somatostatin, growth hormone, secretin, gastrin, vaspressin, oxytocin, glucagon, adrenocorticotropic hormone (ACTH), thyroid-stimulating hormone (TSH), prolactin, luteinizing hormone-releasing hormone (LH-RH), endorphin, enkephalin, neurotensin, lymphokine or monokine such as interferon and interleukin, enzymes such as superoxide dismutase and derivatives and salts thereof. Besides, known peptide hormones, proteins and enzymes having a molecular weight of up to about 30,000 are also included.

Among the above physiologically active peptides, preferred are peptides or derivatives thereof having a molecular weight within the range of 1,000 –10,000. More preferred are calcitonins, parathyroid hormones (PTH) and insulins.

The calcitonins may be peptides having hypocalcemic activity and include various natural calcitonins and pharmaceutically active derivatives thereof. Examples of the natural calcitonins are eel calcitonin, human calcitonin, salmon calcitonin, porcine calcitonin and chicken calcitonin. Examples of the phamaceutically active derivatives thereof are $[ASU^{1,7}]$ eel calcitonin (general name: elcatonin), $[ASU^{1,7}]$ salmon calcitonin, $[ASU^{1,7}]$ human calcitonin and $[ASU^{1,7}]$ chicken calcitonin. Especially preferred is elcatonin.

These substances can be prepared by the processes disclosed, for example, in British Patent No. 1516947 and preliminary manuscript collection of lecture II, page 947 for the 50th Spring Meeting of Japan Chemical Society, in 1985. Moreover, other calcitonin-like peptides having hypocalcemic activity can also be used in this invention. The calcitonin participates in disorder of bones, endocrine and digestive organs and are used for treatment of hypercalcemia, pains in osteoporosis and Paget's disease.

Concentration of calcitonin in the composition of this invention is normally 0.1 U/mg–100 U/mg, preferably 1 U/mg–50 U/mg. Dosage is preferably 10–50 mg/time and number of administration is suitably 1-3 times a day.

The PTH are peptides having hypercalcemic activity and 34-84 amino acid sequences and include natural PTH and pharmaceutically active derivatives thereof. As examples thereof, mention may be made of human-PTH (h-PTH) (1-84) [Biochemistry 17, 5723 (1978)], h-PTH (1-38) [Japanese Patent Kokai No. 57 - 81448], h-PTH (1-34) [Hoppe-Seyler's Z. Phsiol. Chem., 355, 415 (1974)], h-PTH (1-34) $NH_2$ [Japanese Patent Kokai No. 58 - 96052], [$Nle^{8,18}$ h-PTH (1-34), [$Nle^{8,18}$, $Tyr^{34}$] h-PTH (1-34) [Japanese Patent Kokai No. 55 - 113753], [$Nle^{8, 18}$] h-PTH (1-34) $NH_2$ [Japanese Patent Kokai No. 61 - 24598], [$Nle^{8, 18}$, $Tyr^{34}$]h-PTH (1-34) $NH_2$ [Japanese Patent Kokai No. 60 - 34996], rat-PTH (1-84) [J. Biol. Chem., 259 (5), 3320 (1984)], rat-PTH (1-34) [Endocrinol., 117 (3), 1230 (1985)], bovine-PTH (1-84) [Am. J. Med., 50, 639 (1971)], bovine-PTH (1-34), bovine-PTH (1-34) $NH_2$ [Pthobiology annual 11, 53 (1981)], etc.

Insulin include human insulin, swine insulin, bovine insulin, horse insulin and sheep insulin.

As the water-soluble organic acids use in this invention, mention may be made of, for example, at least one of succinic acid, tartaric acid, citric acid, fumaric acid, maleic acid, malonic acid, glutaric acid, adipic acid, malic acid, L-glutamic acid, L-aspartic acid, gluconic acid and glucuronic acid.

In this invention, diluents are used, if necessary. The diluents used in this invention are water-soluble or sparingly soluble and examples thereof are saccharoses, polysaccharides, dextrins, celluloses, synthetic or semisynthetic polymers, amino acids, polyamino acids, proteins and phospholipids.

The succharoses (monosaccharides, oligosaccharides) include, for example, D-mannitol, glucose, lactose, fructose, inositol and sucrose. The polysaccharides include, for example, dextran, pullulan, alginic acid, hyaluronic acid, pectic acid, phytic acid and phytin. The dextrins include, for example, α-cyclodextrin, β-cyclodextrin, γ-cyclodextrin, dextrin, hydroxypropyl starch and hydroxyethyl starch.

The celluloses include, for example, methyl cellulose, ethyl cellulose, hydroxyethyl cellulose, hydroxypropyl cellulose, hydroxypropylmethyl cellulose and sodium carboxymethyl cellulose.

The synthetic and semisynthetic polymers include, for example, polyvinyl alcohol, carboxyvinyl polymer, polyethylene glycol, polyvinylpyrolidone (PVP), sodium polyacrylate and polylactic acid.

The amino acids include, for example, glycine and taurine. The polyamino acids include, for example, polyglutamic acid, polyaspartic acid, polyglycine and polyleucine.

The proteins include, for example, gelatin and chitin and chitosan.

Of these diluents, especially preferred are α-cyclodextrin, β-cyclodextrin, dextrin, D-mannitol, inositol, lactose, dextran, methyl cellulose, hydroxypropyl cellulose, polyvinyl alcohol and pullulan.

The proportion of the components in the powdered composition of this invention varies depending on the kind of the component, but normally is a physiologically active peptide: about 0.005-20 % by weight, preferably about 0.01-10 % by weight, water-soluble organic acid: about 0.05-99.995 % by weight, preferably about 0.5-99.99 % by weight and diluent: about 0.05-99.5 % by weight which is added, if necessary.

The water-soluble organic acid is at least in such an amount that the aqueous solution of the powdered composition is acidic and may be optionally determined depending on clinical uses. One preference is that water-soluble organic acid is added until the pH is not more than about 4 when the composition (10 mg) is dissolved in water (1 ml).

In addition, additives required for formulation of the powdered preparation can be added, if necessary.

The nasal administration powdered composition of this invention can be prepared by known methods.

For instance, water-soluble organic acid and, if necessary, diluent are added to peptide, followed by mixing. Alternatively, a mixture of peptide, water-soluble organic acid and, if necessary, diluent is once after, the mixture is ground to obtain a nasal administration powdered composition. Alternatively, peptide and water-soluble organic acid are once dissolved in a distilled water and lyophilized and then ground to obtain a powder, to which, if necessary, diluent or a mixture of diluent and water-soluble organic acid is added. Or, peptide and diluent are once dissolved in a distilled water and lyophilized and then ground to powder. To the resulting lyophilized powder is added water-soluble organic acid or are added water-soluble organic acid and diluent,and these are mixed to obtain a homogeneous composition.

The resulting powdered composition is superior in solubility and so the particle size of the components is not critical, but preferably 80 % or more of the composition have 300 microns or less. Especially, if 80 % or more is dispersed in the range of 5-200 microns, durability can be somewhat improved.

The powdered composition of this invention is used, for example, in the following manner. That is, the composition is filled in a capsule. This capsule is fixed in a spraying container for nasal administration and small holes are pricked by a needle at both ends of the capsule on use. Then, air is blown thereinto to jet the powdered composition into nasal cavity. However, method of the administration is not critical.

The nasal administration powdered composition of this invention is superior to the conventional liquid preparations for nasal administration of peptide hormone in in terms of stability of active ingredient. Further, in the conventional liquid preparations for nasal administration of peptide hormone, surface active agents are used as absorption promoter, which are highly irritative against nasal mucosa and besides, preservatives are used for preventing contamination with microorganisms, which cause harmful effects. On the other hand, preparations comprising the nasal administration powdered composition of this invention suffer from no such problems.

In addition, the nasal administration powdered composition of this invention is much superior to the conventional nasal administration powdered preparations in absorbability through nasal mucosa.

The following nonlimiting examples and experimental examples explain this invention in more detail.

EXAMPLE 1

(a) 50 Ml of distilled water was added to 10,000 units of elcatonin and 2.0 g of D-glucuronic acid to dissolve them. Then, the solution was lyophilized to obtain a uniform lyophilized product. This product was put in a mortar and ground to obtain a powdered preparation. The resulting powder preparation contained 5 U/mg of elcatonin. This powder preparation is to be used as a nasal administration powdered preparation.

(b) 50 Ml of distilled water was added to 10,000 units of elcatonin and 2.0 g of succinic acid to dissolve them. Then, the solution was lyophilized to obtain a uniform lyophilized product. This product was put in a mortar and ground to obtain a powdered preparation. The resulting powdered preparation contained 5 U/mg of elcatonin. This powdered preparation is used as a nasal administration powdered preparation.

EXAMPLE 2

(a) 50,000 U of elcatonin (6,000 U/mg) and 491.4 mg of D-mannitol were taken in a beaker and 25 ml of distilled water was added thereto to dissolve them. The solution was lyophilized and ground in a mortar to obtain uniform lyophilized powder containing 100 U/mg of elcatonin.

Preparation 1

Then, 20 mg of the resulting lyophilized powder (containing D-mannitol) having 100 U/mg of elcatonin and 100 mg of D-glucuronic acid were taken in a mortar and well mixed and thereto was added gradually 880 mg of dextran (manufactured by Sigma Co. and having an average molecular weight of 40,200) with mixing to obtain a uniform powdered preparation. The resulting powdered preparation contained 2 U/mg of elcatonin. This is used as a nasal administration powdered preparation as described hereinafter.

Preparation 2

20 Mg of the lyophilized powder (containing D-mannitol) obtained in the above (a) and containing 100 U/mg of elcatonin and 200 mg of D-glucuronic acid were taken in a mortar and well mixed and thereto was gradually added 780 mg of dextran (manufactured by Sigma Co. and having an average molecular weight of 40,200) with mixing to obtain a uniform powdered preparation. The resulting powder preparation contained 2 U/mg of elcatonin and was used as a nasal administration powder preparation.

Preparation 3

20 Mg of the lyophilized powder (containing D-mannitol) obtained in the above (a) and containing 100 U/mg of elcatonin and 500 mg of D-glucuronic acid were taken in a mortar and well mixed and thereto was gradually added 480 mg of dextran (manufactured by Sigma Co. and having an average molecular weight of 40,200) with mixing to obtain a uniform powdered preparation. The resulting powdered preparation contained 2 U/mg of elcatonin and was used as a nasal administration powdered preparation.

Preparation 4

20 Mg of the lyophilized powder obtained in the above (a) and containing 100 U/mg of elcatonin was taken in a mortar and thereto was gradually added 980 mg of dextran (manufactured by Sigma Co. and having an average molecular weight of 40,200) with mixing to obtain a uniform powdered preparation which was a control containing no organic acid for comparison with the preparation of this invention. The resulting powdered preparation contained 2 U/mg of elcatonin.

Experimental Methods Example 1

(a) Experiment for Absorption of an Elcatonin Nasal Administration Preparation through Nasal Mucosa in Rabbits.

To Japanese White strain male rabbits (body weight: about 3 kg, one group consisting of 5 rabbits) which had been fasted overnight and anesthetized were administered nasally the preparations 1 and 2 (5 U/2.5 mg/kg) prepared in absorption tests. To the rabbits was administered similarly preparation 4 (control with no D-glucuronic acid) prepared in Example 2 for comparison.

2 Ml of blood was taken from an ea vein before the administration and at 1, 2, 3, 4 and 6 hours after the administration. These blood samples were centrifuged at 3000 rpm for 10 minutes to obtain plasma. Calcium concentration in plasma was determined by an atomic absorptiometer.

(b) Results

After administration of elcatonin nasal administration preparation, calcium concentration in plasma was measured to examine absorption of elcatonin through nasal mucosa. The results are shown in FIG. 1. The preparations of this invention gave remarkable reduction of calcium concentration in plasma after administration as compared with the control preparation with no D-glucuronic acid. The results indicate that absorption of the preparations of this invention through nasal mucosa is markedly enhanced by the addition of D-glucuronic acid as an absorption promoter.

EXAMPLE 3

5000 Units of elcatonin and 500 mg of adipic acid were dissolved in 10 ml of distilled water and the solution was lyophilized to obtain uniform adipic acid (lyophilized powder) containing 10 U/mg of elcatonin. 100 Mg of the resulting adipic acid (lyophilized powder) containing 10 U/mg of elcatonin was put in a mortar and was well mixed while gradually adding 400 mg of previously ground adipic acid to obtain a uniform powdered preparation. The resulting powdered preparation contained 2 U/mg of elcatonin. This powdered preparation and all of the following powdered preparations are similarly used as nasal administration powdered preparations.

EXAMPLE 4

5,000 Units of elcatonin and 2.0 g of L-glutamic acid were dissolved in 200 ml of distilled water and lyophilized to obtain L-glutamic acid (lyophilized product) containing 2.5 U/mg of elcatonin. This lyophilized product was taken in a mortar and ground to obtain a powdered preparation.

EXAMPLE 5

5,000 Units of elcatonin and 50 mg of D-mannitol were dissolved in 5 ml of distilled water and lyophilized to obtain D-mannitol (lyophilized powder) containing 100 U/mg of elcatonin.

10 Mg of the resulting D-mannitol (lyophilized powder) containing 100 U/mg of elcatonin and 100 mg of previously finely ground tartaric acid were taken in a mortar and well mixed and then thereto was gradually added 390 mg of finely ground pullulan (PI - 20, manufactured by Hayashibara Seibutsu Kagaku Kenkyusho) with mixing to obtain a uniform powdered preparation.

The resulting powdered preparation contained 2 U/mg of elcatonin.

EXAMPLE 6

5,000 Units of salmon calcitonin (4,000 U/mg) and 1.0 g of L-glutamic acid were dissolved in 100 ml of distilled water and the solution was lyophilized. The resulting lyophilized product was ground to obtain a powdered preparation containing 5 U/mg of salmon calcitonin.

EXAMPLE 7

5 Ml of distilled water and added to 50 mg of D-mannitol (special grade chemical manufactured by Wako Junyaku Co.) and 5,000 units (6,000 U/mg) of elcatonin to dissolve them. Then, the solution was lyophilized to obtain a uniform powder containing 100 U/mg of elcatonin.

Separately, 50 ml of distilled water was added to each of 500 mg of succinic acid (special grade chemical manufactured by Wako Junyaku Co.) and 500 mg of D-mannitol. Each of the resulting solutions was lyophilized. The resulting powder was ground in a mortar to obtain lyophilized powder of succinic acid and lyophilized powder of D-mannitol.

The following preparation 5 was produced from these lyophilized powders.

Production of Preparation 5

10 Mg of the D-mannitol (lyophilized powder) containing 100 U/mg of elcatonin obtained above and 50 mg of succinic acid (lyophilized powder) obtained above were taken in a mortar and well mixed and then thereto was gradually added 440 mg of hydroxypropyl cellulose (HPC-L manufactured by Nippon Soda Co., Ltd.) with mixing. The resulting powdered preparation contained 2 U/mg of elcatonin.

In the same manner, a blank preparation was prepared as a control using 50 mg of mannitol (lyophilized powder) obtained above in place of succinic acid (lyophilized powder).

Absorption Tests (a) Experiment for Nasal Administration of an Elcatonin Nasal Administration Preparation in Rabbits.

To Japanese White strain male rabbits (body weight: about 3 kg, one group consisting of 5 rabbits) which had been fasted overnight and anesthetized were administered nasally the elcatonin nasal administration powdered preparation (4 U/2 mg/kg) of preparation 5 prepared in Example 7.

In the same manner as for the preparation 5, the blank preparation prepared in Example 7 as a control which contained 2 U/mg of elcatonin, but contained no succinic acid was administered.

2 Ml of blood was taken from an ear vein before the administration and at 1, 2, 3, 4 and 6 hours after the administration. These blood samples were centrifuged at 3,000 rpm for 10 minutes to obtain plasma.

Calcium concentration in plasma was determined by atomic absorptiometer.

The calcium concentration in plasma taken at 5 minutes before the administration was taken as standard value (100 %).

(b) Results

Figure 2:
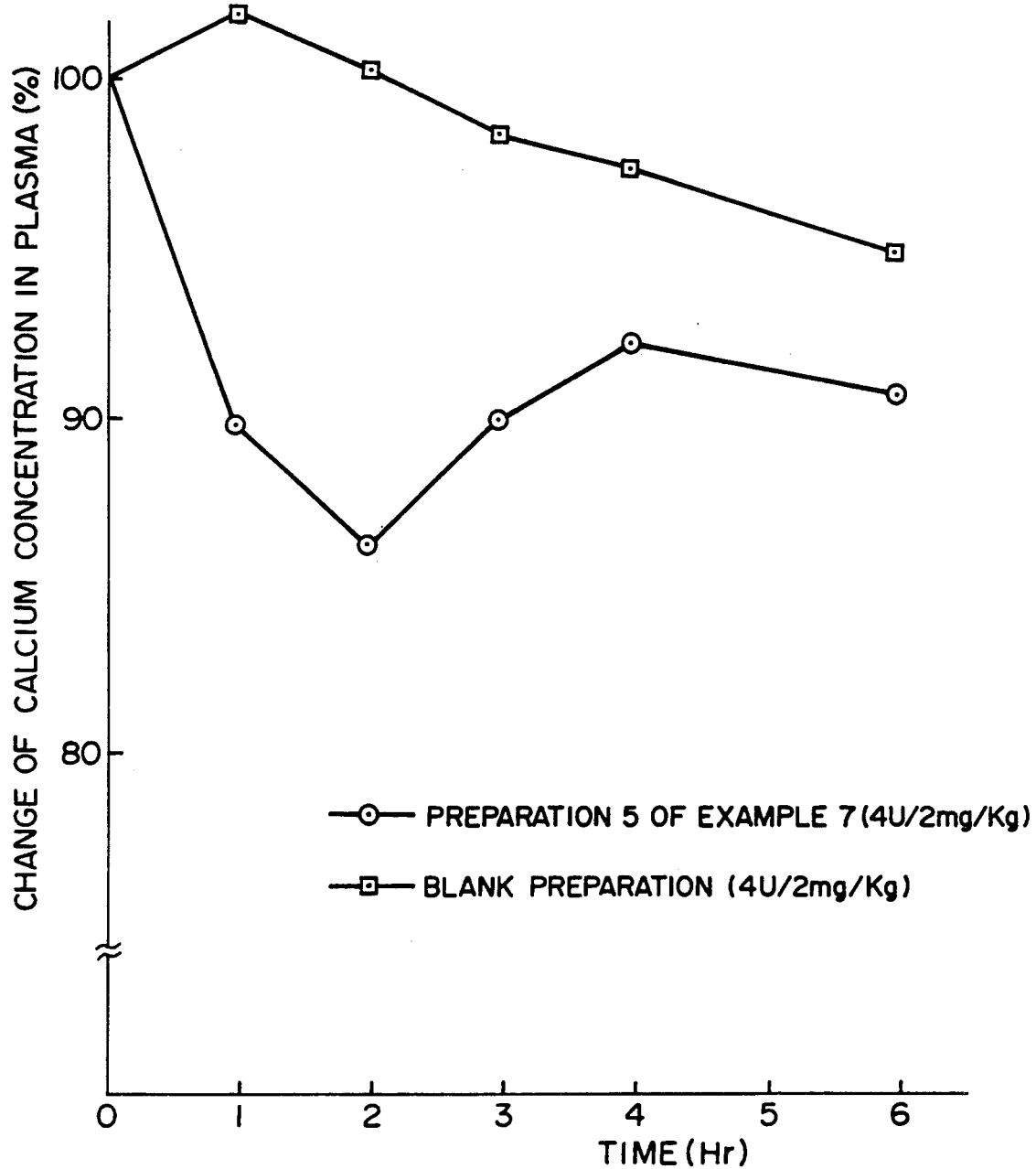
FIG. 2 is a graph which shows changes in calcium concentration in plasma of rabbits when preparation 5 obtained in Example 7 of this invention was administered to rabbits according to the experimental method of Example 7.

The results are shown in FIG. 2, in which changes of calcium concentration in plasma after nasal administration are shown for the blank preparation (4 U/2 mg/kg) (-□-) and preparation 5 (4 U/2 mg/kg) (-○-).

It can be seen from the figure that calcium concentration in plasma was significantly decreased by addition of the water-soluble organic acid as compared with the results obtained by use of the blank preparation.

EXAMPLE 8

5,000 Units of elcatonin and 250 mg of succinic acid were dissolved in 25 ml of distilled water and lyophilized to obtain succinic acid (lyophilized powder) containing 20 U/mg of elcatonin.

50 Mg of the resulting succinic acid (lyophilized powder) containing 20 U/mg of elcatonin was taken in a mortar and well mixed with gradual addition of 450 mg of hydroxypropyl cellulose (HPC-L, manufactured by Nippon Soda Co., Ltd.) to obtain a uniform powdered preparation.

The resulting powder preparation contained 2 U/mg of elcatonin.

10–50 Mg of this powder preparation was filled in a capsule to obtain a preparation for nasal administration for humans.

EXAMPLE 9

5,000 Units of elcatonin and 50 mg of D-mannitol were dissolved in 5 ml of distilled water and lyophilized to obtain D-mannitol (lyophilized powder) containing 100 U/mg of elcatonin. 10 Mg of the resulting D-mannitol (lyophilized powder) containing 100 U/mg of elcatonin and 50 mg of previously finely ground succinic acid were taken in a mortar and well mixed. Then, mixing was effected with gradual addition of 440 mg of hydroxypropyl cellulose (HPC-L, manufactured by Nippon Soda Co., Ltd.) to obtain a uniform powder preparation.

This powder preparation contained 2 U/mg of elcatonin.

10–50 Mg of this powder preparation was filled in a capsule to obtain a nasal administration preparation for humans

EXAMPLE 10

5,000 Units (4,000 U/mg) of salmon calcitonin and 250 mg of L-glutamic acid were dissolved in 25 ml of distilled water and lyophilized to obtain L-glutamic acid (lyophilized powder) containing 20 U/mg of salmon calcitonin.

50 Mg of the resulting L-glutamic acid (lyophilized powder) containing 20 U/mg of salmon calcitonin was taken in a mortar and well mixed with gradual addition of 450 mg of dextran (having an average molecular weight of 40,200, manufactured by Sigma Co.) to obtain a unifirm powder preparation.

EXAMPLE 11

5,000 Units of salmon calcitonin, 125 mg of adipic acid and 875 mg of inositol were taken in a beaker and thereto was added 100 ml of distilled water to dissolve them. The solution was lyophilized to obtain a lyophilized solid. This was taken in a mortar and ground to obtain a powder composition containing salmon calcitonin (5 U/mg).

EXAMPLE 12

5,000 Units of h-PTH (1–34) and 250 mg of glycine were dissolved in 25 ml of distilled water and lyophilized to obtain glycine (lyophilized powder) containing 20 units of h-PTH (1-34).

100 Mg of the resulting glycine (lyophilized powder) containing 20 U/mg of h-PTH (1-34) was taken in a mortar and well mixed with gradual addition of 300 mg of previously finely ground tartaric acid to obtain a uniform powder preparation.

EXAMPLE 13

(a) 100 Mg of porcine insulin sodium salt (CALBIO-CHEM ®, specific activity: 26.3 U/mg, water content: 9.88 %) was taken in a mortar and mixed with gradual addition of 900 mg of D-glucuronic acid to obtain a uniform insulin powder preparation. The resulting powder preparation contained 2.37 U/mg of insulin.

(b) 100 Mg of porcine insulin sodium salt (CALBIO-CHEM ®, specific activity: 26.3 U/mg, water content: 9.88 %) was taken in a mortar and mixed with gradual addition of 900 mg of adipic acid to obtain a uniform insulin powder preparation. The resulting powder preparation contained 2.37 U/mg of insulin.

(c) 100 Mg of pocine insulin sodium salt (CALBIO-CHEM ®, specific activity 26.3 U/mg, water content: 9.88 %) was taken in a mortar and mixed with gradual additon of 900 mg of citric anhydride to obtain a uniform insulin powder preparation. The resulting powder preparation contained 2.37 U/mg of insulin.

EXAMPLE 14

(a) 100 Mg of porcine insulin sodium salt (CALBIO-CHEM ®, specific activity: 26.3 U/mg, water content: 9.88 %) and 100 mg of D-glucuronic acid were taken in a mortar and well mixed and then mixed with gradual addition of 800 mg of dextran (average molecular weight: 40,200, manufactured by Sigma Co.) as a diluent to obtain a uniform powder preparation. The resulting powder preparation contained 2.37 U/mg of insulin.

(b) 100 Mg of porcine insulin sodium salt (CALBIO-CHEM ®, specific activity: 26.3 U/mg, water content: 9.88 %) and 200 mg of D-glucuronic acid were taken in a mortar and well mixed and then mixed with gradual addition of 700 mg of dextran (average molecular weight: 40,200, manufactured by Sigma Co.) as a diluent to obtain a uniform powder preparation. The resulting powder preparation contained 2.37 U/mg of insulin.

(c) 100 Mg of porcine insulin sodium salt (CALBIO-CHEM ®, specific activity: 26.3 U/mg, water content: 9.88 %) and 300 mg of D-glucuronic acid were taken in a mortar and well mixed and then mixed with gradual addition of 600 mg of dextran (average molecular weight: 40,200, manufactured by Sigma Co.) as a diluent to obtain a uniform powder preparation. The resulting powder preparation contained 2.37 U/mg of insulin.

(d) 100 Mg of porcine insulin sodium salt (CALBIO-CHEM ®, specific activity: 26.3 U/mg, water content: 9.88 %) and 200 mg of succinic acid were taken in a mortar and well mixed and then mixed with gradual addition of 700 mg of dextran (average molecular weight: 40,200, manufactured by Sigma Co.) as a diluent to obtain a uniform powder preparation. The resulting powder preparation contained 2.37 U/mg of insulin.

(e) 100 Mg of porcine insulin sodium salt (CALBIO-CHEM ®, specific activity: 26.3 U/mg, water content: 9.88 %) and 200 mg of tartaric acid were taken in a mortar and well mixed and then mixed with gradual addition of 700 mg of dextran (average molecular weight: 40,200, manufactured by Sigma Co.) as a diluent to obtain a un powder preparation. The resulting powder pre contained 2.37 U/mg of insulin.

(f) 100 Mg of porcine insulin sodium salt (CALBIO-CHEM ®, specific activity: 26.3 U/mg, water content: 9.88 %) and 200 mg of citric anhydride were taken in a mortar and well mixed and then mixed with gradual addition of 700 mg of dextran (average molecular weight: 40,200, manufactured by Sigma Co.) as a diluent to obtain a uniform powder preparation. The resulting powder preparation contained 2.37 U/mg of insulin.

(g) 100 Mg of porcine insulin sodium salt (CALBIO-CHEM ®, specific activity: 26.3 U/mg, water content: 9.88 %) was taken in a mortar and mixed with gradual addition of 900 mg of dextran (average molecular weight: 40,200, manufactured by Sigma Co.) to obtain a uniform powder preparation containing no organic acid as a control preparation for comparison. The resulting powder preparation contained 2.37 U/mg of insulin.

Absorption Tests (a) Experiment for Nasal Administration of an Insulin Nasal Administration Preparation in Rabbits.

To Japanese White strain male rabbits (body weight: about 3 kg, one group consisting of 5 rabbits) which had been fasted for 17 hours before administration and anesthetized with pentobarbital (25 mg/kg) were administered nasally 5 U/2.1 mg/kg with the preparation 6 of Example 14 or the control preparation obtained in Example 14.

2 Ml of blood was drawn from an ear vein 5 minutes before the administration and 30 minutes, 1 hour, 2 hours, 3 hours, 4 hours and 6 hours after the administration. These blood samples were centrifuged at 3,000 rpm for 10 minutes to obtain plasma.

Evaluation on absorbability of the insulin preparation through nasal mucosa was carried out by measuring decrease of glucose concentration in plasma. The glucose concentration in plasma was measured by using a kit of clinical test chemicals Glucose-Test Wako (Wako Junyaku Co.).

The glucose concentration in the plasma obtained for the blood drawn before the administration was taken as the standard value (100 %) for glucose concentration in serum.

(b) Results

Figure 3:
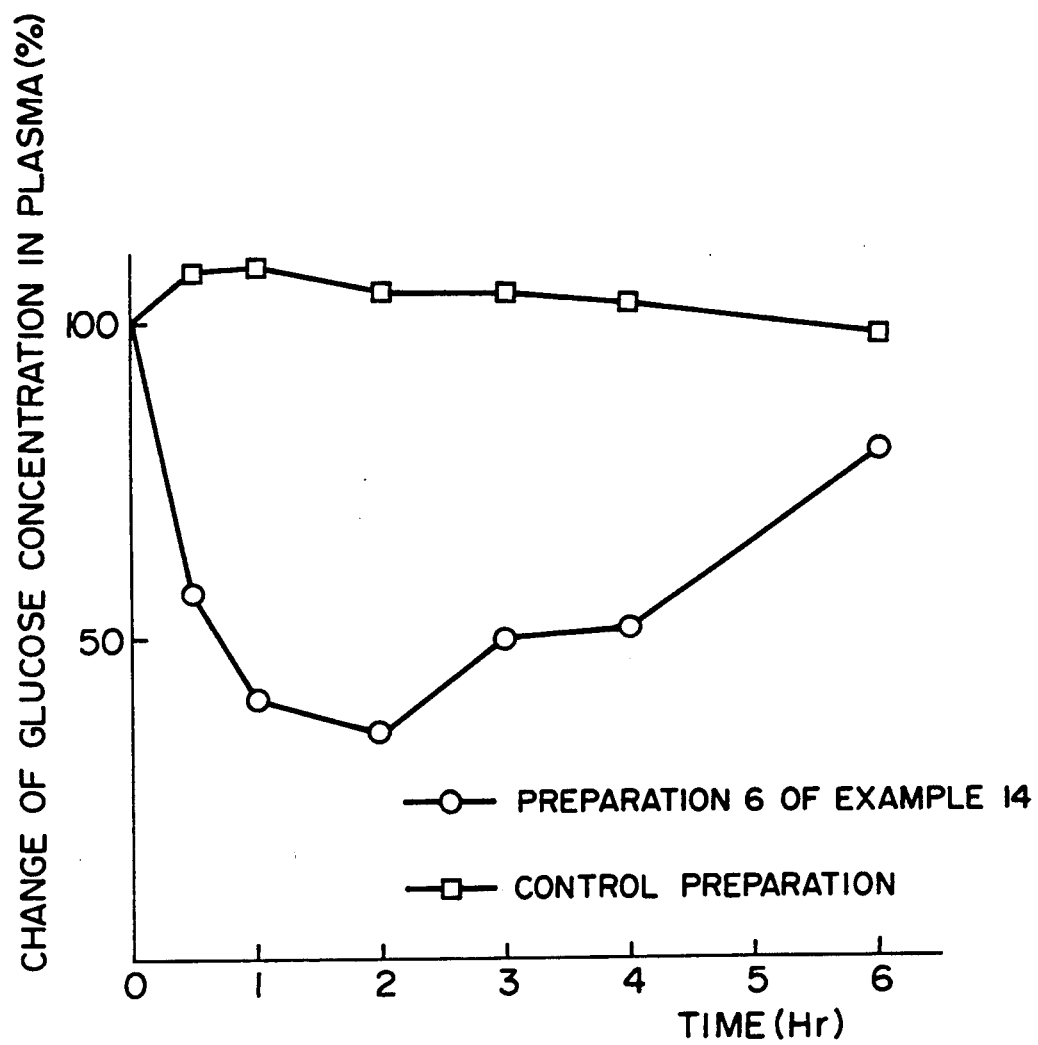
FIG. 3 is a graph which shows changes in glucose concentration in plasma of rabbits when preparation 6 obtained in Example 14 of this invention was administered to rabbits according to the method of Example 14.

The results are shown in FIG. 3. That is, FIG. 3 shows changes of glucose concentration in plasma after nasal administration of the insulin powder preparation 6 of this invention (indicated by -○-) and the control preparation (indicated by -□-).

The results shown in FIG. 3 indicate that insulin was more efficiently absorbed through the nasal mucosa by addition of D-glucuronic acid as an absorption promoter as compared with the control preparation.

EXAMPLE 15

50,000 Units of elcatonin and 190 mg of D-mannitol were taken in a beaker and 10 ml of water was added thereto to dissolve them. The resulting solution was lyophilized and ground in a mortar to obtain a uniform lyophilized powder containing 250 U/mg of elcatonin.

(a) 20 Mg of the above obtained lyophilized powder containing 250 U/mg of elcatonin and 200 mg of D-glucuronic acid were taken in a mortar and well mixed and then thereto was added 780 mg of dextran (average molecular weight: 66,300, manufactured by Sigma Co.) with mixing to obtain a uniform powder preparation. 20

Mg of the preparation was filled in a No. 2 capsule. This capsule preparation contained 100 units of elcatonin per capsule. Actual administration was performed by fixing the capsule in a spray container, pricking holes at both ends of the capsule and blowing air thereinto to administer the powder from the tip of the capsul into nasal cavity.

(b) 40 Mg of the above lyophilized powder containing 250 U/mg of elcatonin and 200 mg of D-glucuronic acid were taken in a mortar and well mixed and then thereto was gradually added 760 mg of pullulan (PI-20) with mixing to obtain a uniform powder preparation. 10-50 Mg of this powder preparation was filled in a No. 2 capsule for nasal administration to obtain a nasal administration preparation for humans. The resulting capsule preparation contained 100-500 units of elcatonin per capsule.

EXAMPLE 16

40,000 Units of h-PTH (1-34) and 190 mg of D-mannitol were taken in a beaker and 10 ml of distilled water was added thereto to dissolve them. The resulting solution was lyophilized and ground in a mortar to obtain a uniform lyophilized powder containing 200 U/mg of h-PTH (1-34).

(a) 20 Mg of the above obtained lyophilized powder containing 200 U/mg of h-PTH (1-34) and 200 mg of D-glucuronic acid were taken in a mortar and well mixed and then thereto was gradually added 780 mg of dextran (average molecular weight: 40,200, manufactured by Sigma Co.) with mixing to obtain a uniform powder preparation. 25 Mg of the preparation was filled in a No. 2 capsule to obtain a nasal administration powder preparation for humans containing 100 units of h-PTH (1-34) per capsule.

(b) 40 Mg of the above obtained lyophilized powder containing 200 U/mg of h-PTH (1-34) and 200 mg of D-glucuronic acid were taken in a mortar and well mixed and then thereto was gradually added 760 mg of hydroxypropyl cellulose (HPC-L manufactured by Nippon Soda Co. Ltd.) with mixing to obtain a uniform powder preparation. 25 Mg and 50 mg of the powder preparations were filled in No. 2 capsules to obtain nasal administration powder preparations for humans which contained 200 units and 400 units of h-PTH (1-34) per capsule, respectively.

EXAMPLE 17

Production of Preparation 17

50 Ml of distilled water was added to 5,000 units of elcatonin and 2.0 g of D-glucuronic acid to dissolve them. Then, the solution was lyophilized to obtain a uniform lyophilized product. This product was put in a mortar and ground to obtain a powder preparation. The resulting powder preparation contained 2.5 U/mg of elcatonin.

A control preparation (elcatonin 2.5 U/mg) was prepared in the same manner as above except that D-mannitol was used in place of D-glucuronic acid.

Production of Preparation 8

50 Ml of distilled water was added to 5,000 units of elcatonin and 2.0 g of succinic acid to dissolve them. Then, the solution was lyophilized to obtain a uniform lyophilized product. This product was put in a mortar and ground to obtain a powder preparation. The resulting powder preparation contained 2.5 U/mg of elcatonin.

Absorption Tests (a) Experiment for Nasal Administration of an Elcatonin Nasal Administration Preparation in Rabbits.

To Japanese White strain male rabbits (body weight: about 3 kg, one group consisting of 5 rabbits) which had been fasted overnight and anesthetized were administered nasally the preparations 7 and 8 (5 U/2 mg/kg) prepared in Example 17. To the rabbits was administered similarly a control prepared in Example 17 (using mannitol in place of organic acid).

2 Ml of blood was taken from an ear vein before the administration and 1, 2, 3, 4 and 6 hours after the administration. These blood samples were centrifuged at 3000 rpm for 10 minutes to obtain plasma. Calcium concentration in plasma was determined by an atomic absorptiometer. The calcium concentration in plasma taken 5 minutes before the administration was used as standard value (100 %) of calcium concentration in plasma.

(b) Results

Figure 4:
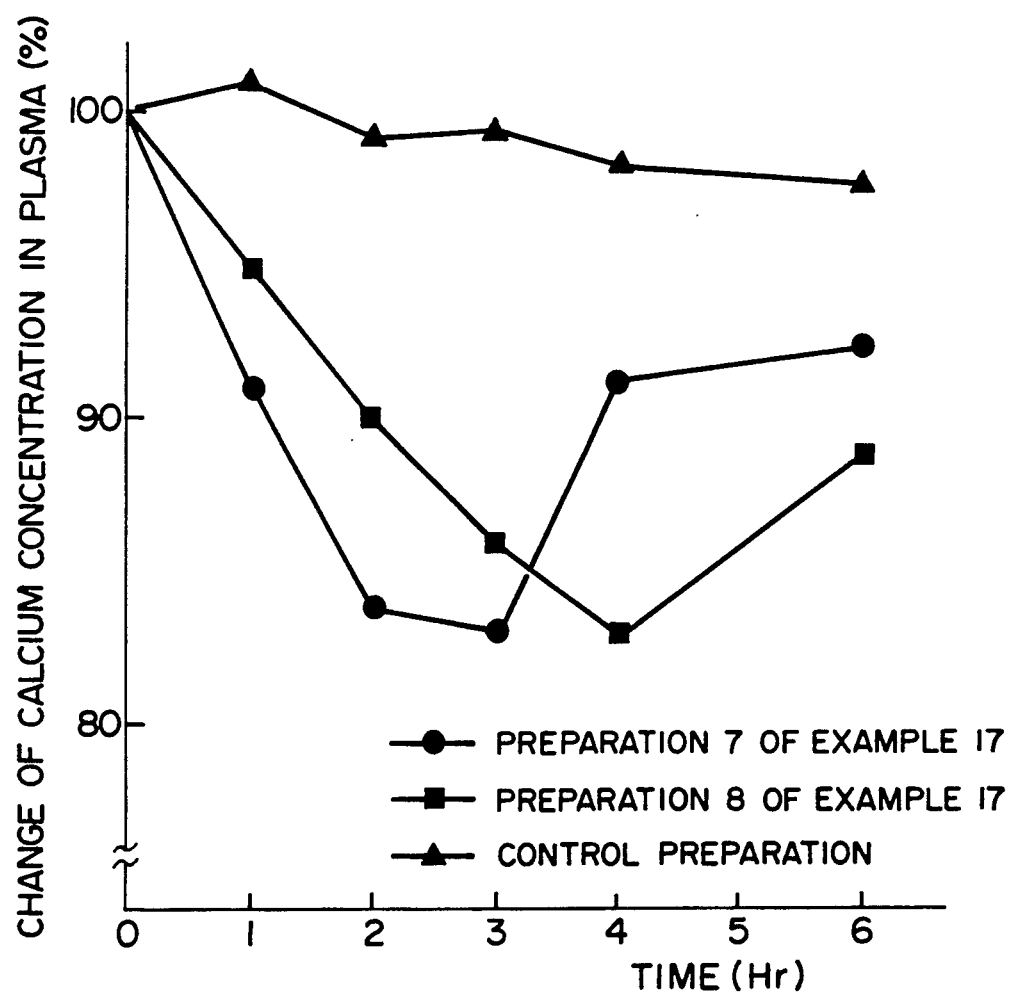
FIG. 4 is a graph which shows changes in calcium concentration in plasma of rabbits when preparations 7 and 8 obtained in Example 17 of this invention were administered to rabbits according to the experimental method of Example 17.

FIG. 4 shows changes of calcium concentration in plasma after administration of the control preparation (5 U/2 mg/kg) (- -) and preparation 7 (5 U/2 mg/kg) (- -) and preparation 8 (5 U/2 mg/kg) (- -).

As is clear from FIG. 4, calcium concentration in plasma was significantly decreased with addition of the water-soluble organic acid as compared with the results obtained using the control preparation.

EXAMPLE 18

Production of Preparation 9

25 Ml of distilled water was added to 5,000 units of human parathyroid hormone 1-34 [h-PTH (1-4)] and 1.0 g of D-glucuronic acid to dissolve them. The solution was lyophilized to obtain a uniform lyophilized product containing 5 U/mg of h-PTH (1-34). The resulting lyophilized product was taken in a mortar and ground to obtain a powder preparation.

Absorption Tests (a) Experiment for Nasal Administration of h-PTH (1-34) in Rabbits Japanese White strain male rabbits (body weight: 3 kg, one group consisting of 5 rabbits) were fasted overnight and then a tube was previously cannulated into one of carotids under anesthetization for.measurement of arterial pressure. The arterial pressure was recorded through a pressure transducer. The h-PTH (1-34) nasal administration preparation of preparation 9 prepared in Example 18 (10 U/2 mg/kg) was nasally administered to the rabbits under anesthetization. Blood pressure was observed for 1 hour from the administration. For comparison, injection preparation of h-PTH (1-34) (3 U/2 mg/kg) was intravenously administered and similarly blood pressure was measured.

(b) Results

The results are shown in Table 1.

TABLE 1

| | Depression rate of blood pressure (%) Minimum blood pressure | | | | | |
|---|---|---|---|---|---|---|
| | Before administration | 30 sec. | 1 min. | 5 min. | 15 min. | 1 hr |
| Preparation 9 10 U/2 mg/kg | 0 | 32 | 45 | 31 | 9 | 1 |
| Intravenous injection 3 U/0.1 ml/kg | 0 | 43 | 40 | 25 | 6 | 3 |

As is clear from Table 1, h-PTH (1–34) can be efficiently absorbed through nasal mucosa by addition of a water-soluble organic acid as an absorption promoter.

As explained above, the nasal administration powder composition of physiologically active peptides according to this invention can be efficiently absorbed through nasal mucosa by the addition of an organic acid as an absorption promoter. Further, the composition is powdered preparation and has safety and stability.

Therefore, according to this invention, practical use of nasal administration powder preparation of physiologically active peptides has become possible.

We claim:

1. A composition being in powder form suitable for nasal administration containing a hypocalcemic effective amount of a peptide having calcitonin activity as an active ingredient and a water-soluble organic acid as an absorption promoter said acid present in an amount sufficient to render acidic an aqueous solution including said composition, said acid being at least one member selected from the group consisting of succinic acid, tartaric acid, and glucuronic acid.

2. A nasal administration powder composition according to claim 1 which additionally contains a diluent.

3. A nasal administration powder composition according to claim 2 wherein the diluent is at least one member selected from the group consisting of monosaccharides, disaccharides, inositol, dextrans, methyl cellulose, ethyl cellulose, hydroxyethyl cellulose, hydroxypropyl cellulose, hydroxypropylmethyl cellulose and glycine.

4. A nasal administration powder composition comprising the composition according to claim 1 wherein the physiologically active peptide is a calcitonin and the water-soluble organic acid is D-glucuronic acid or succinic acid.

5. The composition of claim 1 said composition having a pH of 4 when 10 mg of said composition are dissolved in 1 ml of water.

6. The composition of cliam 1 wherein the composition copmrises powder particles at least 80% of which are less than 300 microns in size.

7. The composition of cliam 6 wherien at least 80% of the particles are between 5 and 200 microns in size.

8. The composition of claim 7 wherein said peptide is calcitonin, said acid is D-glucuronic acid and said diluent is selected from the group consisting of mannitol and dextran.

9. The composition of claim 8 wherein said peptide is calcitonin, said acid is D-glucuronic acid and said diluent is dextran.

10. A nasal administration powder according to claim 2 wherein said diluent is selected from the group consisting of D-mannitol, dextran, hydroxypropyl cellulose and glycine.

* * * * *